(12) United States Patent
Iwatani et al.

(10) Patent No.: US 7,555,392 B2
(45) Date of Patent: Jun. 30, 2009

(54) METHOD FOR DETERMINING METABOLIC FLUX

(75) Inventors: Shintaro Iwatani, Kawasaki (JP); Stephen Van Dien, Kawasaki (JP); Yoshihiro Usuda, Kawasaki (JP); Kazuhiko Matsui, Kawasaki (JP)

(73) Assignee: Ajinomoto Co., Inc., Tokyo (JP)

( * ) Notice: Subject to any disclaimer, the term of this patent is extended or adjusted under 35 U.S.C. 154(b) by 290 days.

(21) Appl. No.: 11/095,521

(22) Filed: Apr. 1, 2005

(65) Prior Publication Data

US 2005/0221278 A1 Oct. 6, 2005

(30) Foreign Application Priority Data

Apr. 2, 2004 (JP) ............................. 2004-109864

(51) Int. Cl.
*G06F 7/00* (2006.01)
(52) U.S. Cl. .............................. 702/19; 702/20; 703/11; 707/102
(58) Field of Classification Search ....................... None
See application file for complete search history.

(56) References Cited

U.S. PATENT DOCUMENTS

2003/0228567 A1* 12/2003 Famili et al. ................... 435/4
2004/0033975 A1* 2/2004 Fu et al. ......................... 514/44

FOREIGN PATENT DOCUMENTS

| WO | WO 00/46405 | | 8/2000 |
|---|---|---|---|
| WO | WO 02/055995 A2 | | 7/2002 |
| WO | WO 02/061115 A2 | | 8/2002 |
| WO | WO03/029425 | * | 4/2003 |
| WO | 2005/010794 | | 2/2005 |

OTHER PUBLICATIONS

Arauzo-Bravo et al. Journal of Biotechnology 105 (2003) 117-133.*
Ross Carlson, "Fundamental *Escherichia coli* Biochemical Pathways for Biomass and Energy Production: Identification of Reactions." Biotechnology and Bioengineering, vol. 85, No. 1, Jan. 5, 2004, pp. 1-19.
Ross Carlson, "Fundamental *Escherichia coli* Biochemical Pathways for Biomass and Energy Production: Creation of Overall Flux States." Biotechnoloy and Bioengineering, vol. 86, No. 2, Apr. 20, 2004, pp. 149-162.
Steffen Klamt, "Flux Analyzer: exploring structure, pathways, and flux distributions in metabolic networks on interactive flux maps." Bioinformatics (Oxford), vol. 19, No. 2, Jan. 22, 2003, pp. 261-269.
Steffen Klamt, "Calculability Analysis in Undetermined Metabolic Networks Illustrated by a Model of the Central Metabolism in Purple Nonsulfer Bacteria," Biotechnology and Bioengineering, vol. 77, No. 7, Mar. 30, 2002, pp. 734-751.
Varma, A. et al. "Stoichiometric Flux Balance Models Quantitatively Predict Growth and Metabolic By-Product Secretion in Wild-Type *Escherichia coli* W3110", *Applied Environmental Microbiology*, vol. 60 (10) pp. 3724-3731, 1994.
Schilling, C.H. et al. "Toward Metabolic Phenomics: Analysis of Genomic Data Using Flux Balances", *Biotechnol. Prog.*, vol. 15 pp. 288-295, 1999.
Schilling, C.H. et al. "Metabolic Pathway Analysis: Basic Concepts and Scientific Applications in the Post-genomic Era", *Biotechnol. Prog.*, vol. 15 pp. 296-303, 1999.
Pramanik, J. et al. "Stoichiometric Model of *Escherichia coli* Metabolism: Incorporation of Growth-Rate Dependant Biomass Composition and Mechanistic Energy Requirements", *Biotechnology and Bioengineering*, vol. 56 (4) pp. 398-421, 1997.
Ibarra, R.U. et al. "*Escherichia coli* K-12 undergoes adaptive evolution to achieve *in silico* predicted optimal growth", *Nature*, vol. 420 pp. 186-189, 2002.
Vallino, J.J. et al. "Metabolic Flux Distributions in *Corynebacterium glutamicum* During Growth and Lysine Overproduction", *Biotechnology and Bioengineering*, vol. 41 pp. 633-646, 1993.
Wiechert, W. "Modeling and simulation: tools for metabolic engineering", *Journal of Biotechnology*, vol. 94 pp. 37-63, 2002.
Wiechert, W. "Minireview-$^{13}$C Metabolic Flux Analysis", *Metabolic Engineering*, vol. 3 pp. 195-206, 2001.

* cited by examiner

*Primary Examiner*—Mary K Zeman
(74) *Attorney, Agent, or Firm*—The Nath Law Group; Susanne M. Hopkins; Ari G. Zytcer

(57) ABSTRACT

A method for determining metabolic flux distribution of a cell, which comprises the steps of:
1) creating a stoichiometric matrix based on formulas of biochemical reactions from a substrate to a product,
2) computing a set of vectors of solutions existing in a solution space which the stoichiometric matrix may have,
3) selecting, from the computed set of vectors of solutions, maximum vectors whose vector elements corresponding to respective substances for which input values can be obtained are maximum, and
4) performing linear combination for the selected vectors in accordance with the following equations to obtain a vector representing metabolic flux distribution:

$$S_{flux} = \sum_{i=1}^{n} a_i \cdot p_i \cdot S(i) + \sum_{i=1}^{n} b_i \cdot q_i \cdot A(i) \quad (I)$$

$$\sum_{i=1}^{n} a_i + \sum_{i=1}^{n} b_i = 1 \quad (II)$$

$S_{flux}$: Vector representing metabolic flux distribution to be determined,
$S(i)$: Vector selected for substance for which inputted value can be obtained,
$A(i)$: Adjustment vector,
$a, b$: Coefficients for linear combination (b may be 0),
$p$: Coefficient for obtaining consistency with input value as numerical value,
$q$: Coefficient of adjustment vector.

12 Claims, 6 Drawing Sheets

METHOD FOR DETERMINING METABOLIC FLUX

BACKGROUND OF THE INVENTION

The present invention relates to a method for determining a metabolic flux, a program for executing the determination method and a recording medium storing the program.

A metabolic flux analysis, which is also referred to as a flux balance analysis, is a technique for predicting intracellular metabolic flux distributions by construction of a stoichiometric model of intracellular biochemical reactions and linear optimization. This technique has been used in research into the abilities of biochemical reaction systems in microorganisms or for predicting intracellular metabolic flux distributions under different external conditions (Varma, A. and Palsson, B. O. Appl. Environ. Microbiol. 60:3724-3731, 1994; Schilling, C. H. et al., Biotechnol. Prog., 15:288-295, 1999; Schilling, C. H. et al., Biotechnol. Prog., 15:296-303, 1999). It has also been reported that a stoichiometric model was constructed for *Escherichia coli* (Pramanik, J. and Keasling, J. D., Biotechnol. Bioeng., 56:398-421, 1997; Ibarra, R. U. et al., Nature, 420:186-189, 2002). Also known is an example of using such a stoichiometric model in metabolic engineering for lysine production for *Corynebacterium glutamicum*, which is used in amino acid production (Vallino, J. J. and Stephanopoulos, G., Biotechnol. Bioeng., 41:633-646, 1993). In addition, a large number of theoretical or experimental methods for metabolic flux analyses and their applications have been reported (Wiechert, W., Journal of Biotechnology, 94:37-63, 2002; Wiechert, W., Metabolic Engineering, 3:195-205, 2001; International Publication No. WO00/46405; International Publication No. WO02/061115; International Publication No. WO02/055995). WO00/46405 discloses a method for predicting a gene required for growth based on a stoichiometric model. WO02/061115 discloses a technique for genetically and evolutionarily changing cells to impart optimal functions to the cells. Further, WO02/055995 discloses a method for applying constraints of qualitative kinetic information, constraints of qualitative metabolic regulation information and constraints based on DNA microarray experimental data under different conditions, to a stoichiometric model. Although all of these are methods for predicting more desirable intracellular metabolic flux distributions, no method has been disclosed for calculating all possible flux distributions satisfying constraints of biological experimental data such as a growth rate and a product production rate.

SUMMARY OF THE INVENTION

An object of the present invention is to provide a method for determining all metabolic fluxes from minimum analytical information obtained by analysis of a sample of microorganism or medium under cultivation, a method for obtaining a range within which all the metabolic fluxes may change when errors of input data are permitted by using the determination method, a program for executing the determination method, and a recording medium storing the program.

In view of the aforementioned object, the inventors of the present invention conducted various researches. As a result, they found that, if a solution space which a stoichiometric matrix created based on formulas of biochemical reactions from a substrate to a product can have, was obtained, and vectors whose vector elements corresponding to respective data adopted as input data selected from experimental data obtainable from analysis of a sample of microorganism or medium under cultivation were maximum were retrieved from the solution space, and such retrieved vectors are linearly synthesized, a vector of a solution corresponding to the input data (metabolic flux distribution) could be obtained. The present invention was accomplished based on this finding, and provides the followings.

(1) A method for determining metabolic flux distribution of a cell, which comprises the steps of:
1) creating a stoichiometric matrix based on formulas of biochemical reactions from a substrate to a product,
2) computing a set of vectors of solutions existing in a solution space which the stoichiometric matrix may have,
3) selecting, from the computed set of vectors of solutions, maximum vectors whose vector elements corresponding to respective substances for which input values can be obtained are maximum, and
4) performing linear combination for the selected vectors in accordance with the following equations to obtain a vector representing metabolic flux distribution:

$$S_{flux} = \sum_{i=1}^{n} a_i \cdot p_i \cdot S(i) + \sum_{i=1}^{n} b_i \cdot q_i \cdot A(i) \quad (I)$$

$$\sum_{i=1}^{n} a_i + \sum_{i=1}^{n} b_i = 1 \quad (II)$$

$S_{flux}$: Vector representing metabolic flux distribution to be determined,
$S(i)$: Vector selected for substance for which inputted value can be obtained,
$A(i)$: Adjustment vector,
a, b: Coefficients for linear combination (b may be 0),
p: Coefficient for obtaining consistency with input value as numerical value,
q: Coefficient of adjustment vector.

(2) A method for determining metabolic flux distribution of a cell, which comprises the steps of:
1) creating a stoichiometric matrix based on formulas of biochemical reactions from a substrate to a product,
2) computing a set of vectors of solutions existing in a solution space which the stoichiometric matrix may have,
3) selecting, from the computed set of vectors of solutions, maximum vectors whose vector elements corresponding to respective substances for which input values can be obtained are maximum and vectors where values of vector elements thereof are within a predetermined range from the values of said corresponding vector elements of the maximum vectors,
4) performing linear combination for each combination of the selected vectors in accordance with the following equations to obtain a vector set representing metabolic flux distribution, and
5) determining fluxes based on distribution of values of vector elements in the vector set:

$$S_{flux} = \sum_{i=1}^{n} a_i \cdot p_i \cdot S(i) + \sum_{i=1}^{n} b_i \cdot q_i \cdot A(i) \quad (I)$$

$$\sum_{i=1}^{n} a_i + \sum_{i=1}^{n} b_i = 1 \quad (II)$$

$S_{flux}$: Vector representing metabolic flux distribution to be determined,

S(i): Vector selected for substance for which input value can be obtained,
A(i): Adjustment vector,
a, b: Coefficients for linear combination (b may be 0),
p: Coefficient for obtaining consistency with input value as numerical value,
q: Coefficient of adjustment vector.

(3) The method according to (1) or (2), wherein the step of computing a set of vectors of solutions existing in a solution space which the stoichiometric matrix may have is performed by computation based on elementary mode.

(4) The method according to any one of (1) to (3), wherein the substances for which input values can be obtained include carbon dioxide.

(5) The method according to (4), wherein the substances for which input values can be obtained consist of an objective product, biomass, carbon dioxide and byproduct, and the linear combination is performed in accordance with the following equations:

$$S_{flux} = \alpha_1 \cdot \text{product} + \alpha_2 \cdot \text{Biomass} + \alpha_3 \cdot CO_{2max} + \sum_{i=1}^{n} \beta_i \cdot \text{byproduct}(i)$$

$$\sum_{i=1}^{3} \alpha_i + \sum_{i=1}^{n} \beta_i = 1$$

$S_{flux}$: Vector representing metabolic flux distribution to be determined,
product: Vector selected for objective product (multiplied by coefficient for obtaining consistency with input value),
Biomass: Vector selected for cell (multiplied by coefficient for obtaining consistency with input value),
$CO_2$: Vector selected for carbon dioxide (multiplied by coefficient for obtaining consistency with input value),
Byproduct(i): Vector selected for byproduct (multiplied by coefficient for obtaining consistency with input value),
$\alpha_i$: Coefficient for linear combination,
$\beta_i$: Coefficient for linear combination.

(6) A program for determining metabolic flux distribution of a cell, which allows a computer to execute a metabolic flux determination method comprising the procedures of:
1) creating a stoichiometric matrix based on formulas of biochemical reactions from a substrate to a product,
2) computing a set of vectors of solutions existing in a solution space which the stoichiometric matrix may have,
3) selecting, from the computed set of vectors of solutions, maximum vectors whose vector elements corresponding to respective substances for which input values can be obtained are maximum, and
4) performing linear combination for the selected vectors in accordance with the following equations to obtain a vector representing metabolic flux distribution:

$$S_{flux} = \sum_{i=1}^{n} a_i \cdot p_i \cdot S(i) + \sum_{i=1}^{n} b_i \cdot q_i \cdot A(i) \quad \text{(I)}$$

$$\sum_{i=1}^{n} a_i + \sum_{i=1}^{n} b_i = 1 \quad \text{(II)}$$

$S_{flux}$: Vector representing metabolic flux distribution to be determined,
S(i): Vector selected for substance for which input value can be obtained,
A(i): Adjustment vector,
a, b: Coefficients for linear combination (b may be 0),
p: Coefficient for obtaining consistency with input value as numerical value,
q: Coefficient of adjustment vector.

(7) A program for determining metabolic flux distribution of a cell, which allows a computer to execute a metabolic flux determination method comprising the procedures of:
1) creating a stoichiometric matrix based on formulas of biochemical reactions from a substrate to a product,
2) computing a set of vectors of solutions existing in a solution space which the stoichiometric matrix may have,
3) selecting, from the computed set of vectors of solutions, maximum vectors whose vector elements corresponding to respective substances for which input values can be obtained are maximum and vectors where values of vector elements thereof are within a predetermined range from the values of said corresponding vector elements of the maximum vectors,
4) performing linear combination for each combination of the selected vectors in accordance with the following equations to obtain a vector set representing metabolic flux distribution, and
5) determining fluxes based on distribution of values of vector elements in the vector set:

$$S_{flux} = \sum_{i=1}^{n} a_i \cdot p_i \cdot S(i) + \sum_{i=1}^{n} b_i \cdot q_i \cdot A(i) \quad \text{(I)}$$

$$\sum_{i=1}^{n} a_i + \sum_{i=1}^{n} b_i = 1 \quad \text{(II)}$$

$S_{flux}$: Vector representing metabolic flux distribution to be determined,
S(i): Vector selected for substance for which input value can be obtained,
A(i): Adjustment vector,
a, b: Coefficients for linear combination (b may be 0),
p: Coefficient for obtaining consistency with input value as numerical value,
q: Coefficient of adjustment vector.

(8) A computer-readable recording medium, which records the program as defined in (6) or (7).

According to the determination method of the present invention, all metabolic fluxes can be determined from minimum analytical information obtained by analysis of a sample of microorganism or medium under cultivation. Further, by using the determination method, a range within which all the metabolic fluxes may change when errors of input data are permitted can be obtained. Thus, they can be easily determined metabolic fluxes useful for predicting methods of modifying cells effective for improving yield or productivity of an objective product or cells in production of substances, of which representative examples are amino acids and nucleic acids, using cells such as those of microorganisms.

DETAILED DESCRIPTION OF THE INVENTION

Figure 1:
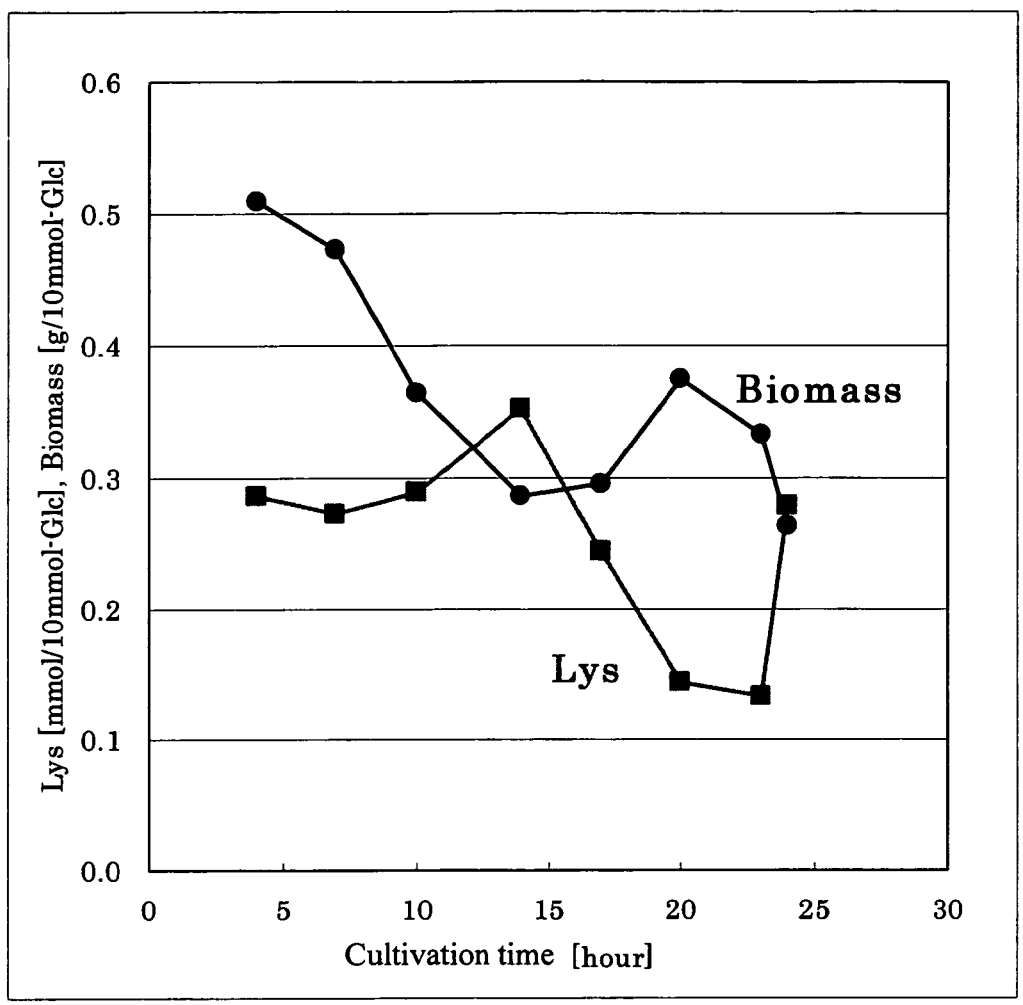
FIG. 1 shows time-course profiles of lysine production and biomass production in a cultivation experiment.

Hereinafter, the present invention will be explained in detail.

<1> Determination Method of the Present Invention

The determination method of the present invention is a method for determining a metabolic flux from only partial analysis information in the substance production using a cell.

The metabolic flux used in the present invention is expressed as a metabolic reaction rate (flux) derived from a stoichiometric model of intracellular biochemical reactions and the law of mass action between metabolites. The metabolic flux distribution is a set of metabolic fluxes and can be represented by a vector in which metabolic fluxes are vector elements.

The cell used in the present invention is not particularly limited so long as it is used in substance production. Examples thereof include various cultured cells, fungi, yeasts, various bacteria and so forth. It is preferably that of a microorganism having an ability to produce a useful compound, for example, an amino acid, a nucleic acid or an organic acid. As the microorganism having an ability to produce an amino acid, a nucleic acid or an organic acid, *Escherichia coli*, *Bacillus* bacteria, coryneform bacteria and so forth are preferably used. A microorganism having an amino acid-producing ability and/or an organic acid-producing ability is more preferred.

In the first step of the determination method of the present invention, a stoichiometric matrix is created based on the biochemical reaction formulas of a substrate to a desired product.

The biochemical reactions refer to a process where intracellular metabolites are converted by enzymatic reactions in the cell, and which have been compiled in various databases according to organism type. For example, Kyoto Encyclopedia of Genes and Genomes (KEGG, www.genome.ad.jp/kegg/) can be accessed for reference.

The substrate is a substance usually used by the cell as a carbon source, and examples thereof include glucose, sucrose, fructose and so forth.

The substance product includes not only a single kind of metabolite, but also an aggregate of metabolites, such as a biomass (cell body). Substance production is usually evaluated as a production rate or yield of a substance. In particular, when the desired substance is a biomass, it is evaluated as a biomass yield. The biomass yield represents efficiency of conversion from substrates such as glucose into cell components such as protein, carbohydrate, nucleic acid or lipid.

The stoichiometric matrix is a matrix usually used in a metabolic flux analysis, and can be created by listing formulas of biochemical reactions of a substrate through a desired product substance by typical methods used in a metabolic flux analysis. Such methods, assuming a quasi-steady state of an intracellular metabolic intermediate, are generally known (Savinell, J. M. and Palsson, B. O. J., Theor. Biol., 154:421-454, 1992; Vallino, J. J. and Stephanopoulos, G., Biotechnol. Bioeng., 41:633-646, 1993). When reaction formulas are listed, reaction pathways may be simplified by assuming a series of reactions without branching as one reaction, or assuming metabolites converted by a reaction at a high metabolic rate before and after the reaction as one metabolite and so forth. When the substance product is a biomass, a stoichiometric matrix can be described by listing biochemical reactions which lead to cell components.

In the second step of the determination method of the present invention, a set of vectors of solutions existing in the solution space defined by the aforementioned stoichiometric matrix is computed. As an example of the method for analyzing a set of specific vectors existing in the solution space, analysis based on the elementary mode can be used (Klamt S., Shuster S., Gilles E. D., Biotechnology and Bioengineering 77, (7):734-51, 2002). An example of the method for obtaining solutions existing in a solution space other than the method mentioned above is a method of selecting independent metabolic fluxes in the same number as the degree of freedom of the defined stoichiometric matrix as free fluxes, producing random combinations of the free fluxes in a number sufficient for a statistical analysis within constraint requirements and computing a solution from each of the produced combinations based on the stoichiometric matrix.

In the third step of the determination method of the present invention, maximum vectors which are vectors in which vector elements corresponding to respective substances for which input values can be obtained are maximum are selected from the set of vectors of solutions computed in the previous step.

Although the input values are not particularly limited, data significantly involved in the carbon balance, for example, analytical data of production rate of an objective product, biomass production rate, carbon dioxide evolution rate etc., are preferred.

The input values include values computed from analytical values obtained in a cultivation experiment based on theoretical and/or experiential knowledge about substance production using cells. For example, if production rate of an objective product and biomass production rate are already obtained as analytical values, and it is known for the cells that most of the output carbon other than the objective product and the cells consists of carbon dioxide, the carbon dioxide evolution rate can be computed from substrate consumption rate, production rate of the objective product and biomass production rate based on the aforementioned knowledge and included in the input values.

The input values are preferably selected considering material balance, in particular, carbon balance. The precision of the determination of metabolic flux distribution can be thereby improved. Examples of the data significantly involved in carbon balance include biomass production rate, carbon dioxide evolution rate and so forth.

A vector element corresponding to a substance for which input value can be obtained means a vector element representing a production rate of the substance.

The vectors to be selected are those in which vector elements corresponding to respective substances for which input values can be obtained are maximum. When the substances for which input values can be obtained are four kinds of substances, an objective product, biomass, carbon dioxide and a byproduct, four kinds of vectors, a vector whose a vector element corresponding to the objective product is maximum, a vector whose a vector element corresponding to the biomass is maximum, a vector whose a vector element corresponding to carbon dioxide is maximum, and a vector whose a vector element corresponding to the byproduct is maximum, are selected.

In the fourth step of the determination method of the present invention, linear combination is performed in accordance with the aforementioned equations (I) and (II) to obtain vectors representing metabolic flux distribution.

The coefficient for obtaining consistency with input value (p in the equations (I) and (II)) is a coefficient for making the vector element corresponding to the substance for which an input value can be obtained coincide with the input value therefore. Although the coefficient is usually equal to a value obtained by dividing the input value with the corresponding vector element, it may be corrected based on theoretical and/or experiential knowledge in substance production using cells. When this coefficient is unnecessary, p takes a value of 1.

The adjustment vector is used for standardizing the whole system (when it is not required, b takes a value of 0 in the equations (I) and (II)). Although the adjustment vector can be chosen based on theoretical and/or experiential knowledge in substance production using cells, it is usually chosen from an aspect of standardization of the material balance. Preferably, a vector relevant to carbon dioxide evolution is used. More preferably, a maximum vector in which evolution of carbon dioxide is maximum is used. This maximum vector can be obtained as a flux vector obtained with simply presupposing that the incorporated substrate is completely oxidized by the TCA cycle.

The adjustment vector may also be multiplied by an appropriate coefficient for modification based on theoretical and/or experiential knowledge about substance production using cells (q in the equations (I) and (II)). When this coefficient is unnecessary, q takes a value of 1.

When the substances for which input values can be obtained are an objective product, biomass, carbon dioxide and a byproduct, and the adjustment vector is not used (that is, b=0), the equations (I) and (II) can be represented as follows.

$$S_{flux} = \alpha_1 \cdot \text{product} + \alpha_2 \cdot \text{Biomass} + \alpha_3 \cdot CO_{2max} + \sum_{i=1}^{n} \beta_i \cdot \text{byproduct}(i)$$

$$\sum_{i=1}^{3} \alpha_i + \sum_{i=1}^{n} \beta_i = 1$$

$S_{flux}$: Vector representing metabolic flux distribution to be determined
product: Vector selected for objective product (multiplied by coefficient for obtaining consistency with input value)
Biomass: Vector selected for cell (multiplied by coefficient for obtaining consistency with input value)
$CO_2$: Vector selected for carbon dioxide (multiplied by coefficient for obtaining consistency with input value)
Byproduct(i): Vector selected for byproduct (multiplied by coefficient for obtaining consistency with input value)
$\alpha_i$: Coefficient for linear combination
$\beta_i$: Coefficient for linear combination Although the vector used for the linear combination is basically a maximum vector, a range of permitted deviation with respect to the maximum vector may be established, and a fluctuation range of a metabolic flux vector can be computed by such an operation. That is, it is also possible that, in the third step, vectors in which a value of any one of vector elements which are the same as the maximum vector elements has a deviation from the corresponding maximum value in the maximum vector within a predetermined range are selected in addition to the maximum vectors whose vector elements corresponding to respective substances for which input values can be obtained are maximum; then linear combination is performed in the same manner as that of the fourth step for each combination of the selected vectors to obtain a vector set representing metabolic flux distribution, and fluxes are determined based on distribution of values of vector elements in the vector set.

The predetermined range may be suitably selected depending on magnitude of errors of the input data, and examples of the range include 99% or more (permitted deviation range of 1%) and 96% or more (permitted deviation range of 4%). The permitted deviation range is usually about 0 to 10%, preferably about 0 to 5%.

Although the mathematical processes in the determination method of the present invention may be individually programmed, they can be easily executed by using mathematical calculation programs such as MatLab® (MathWorks) and Mathematica® (Wolfram Research).

<2> Program of the Present Invention

The program of the present invention is a program for determining metabolic flux distribution of a cell, which allows a computer to execute a metabolic flux determination method comprising the procedures of:

1) creating a stoichiometric matrix based on formulas of biochemical reactions from a substrate to a product,
2) computing a set of vectors of solutions existing in a solution space which the stoichiometric matrix can have,
3) selecting, from the computed set of vectors of solutions, maximum vectors which are vectors in which vector elements corresponding to respective substances for which input values can be obtained are maximum, and
4) performing linear combination for the selected vectors in accordance with the following equations to obtain a vector representing metabolic flux distribution.

Figure 5:
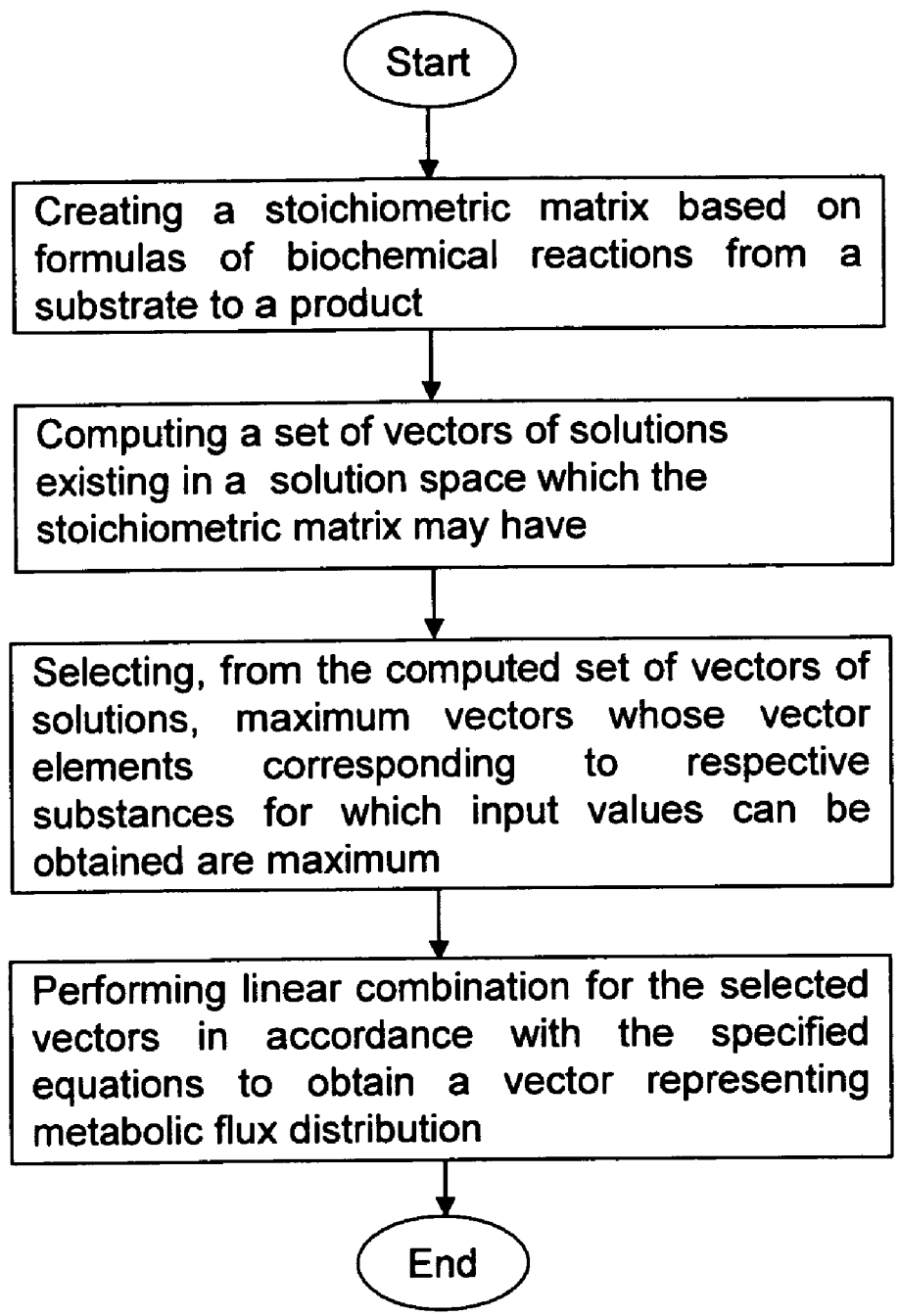
FIG. 5 shows a flowchart of an embodiment of the program of the present invention.

A flowchart of the program of the present invention is shown in FIG. 5. Each procedure is a procedure for executing each of the first to fourth steps of the determination method of the present invention. The program for allowing a computer to execute these procedures can be created according to a usual programming method.

Figure 6:
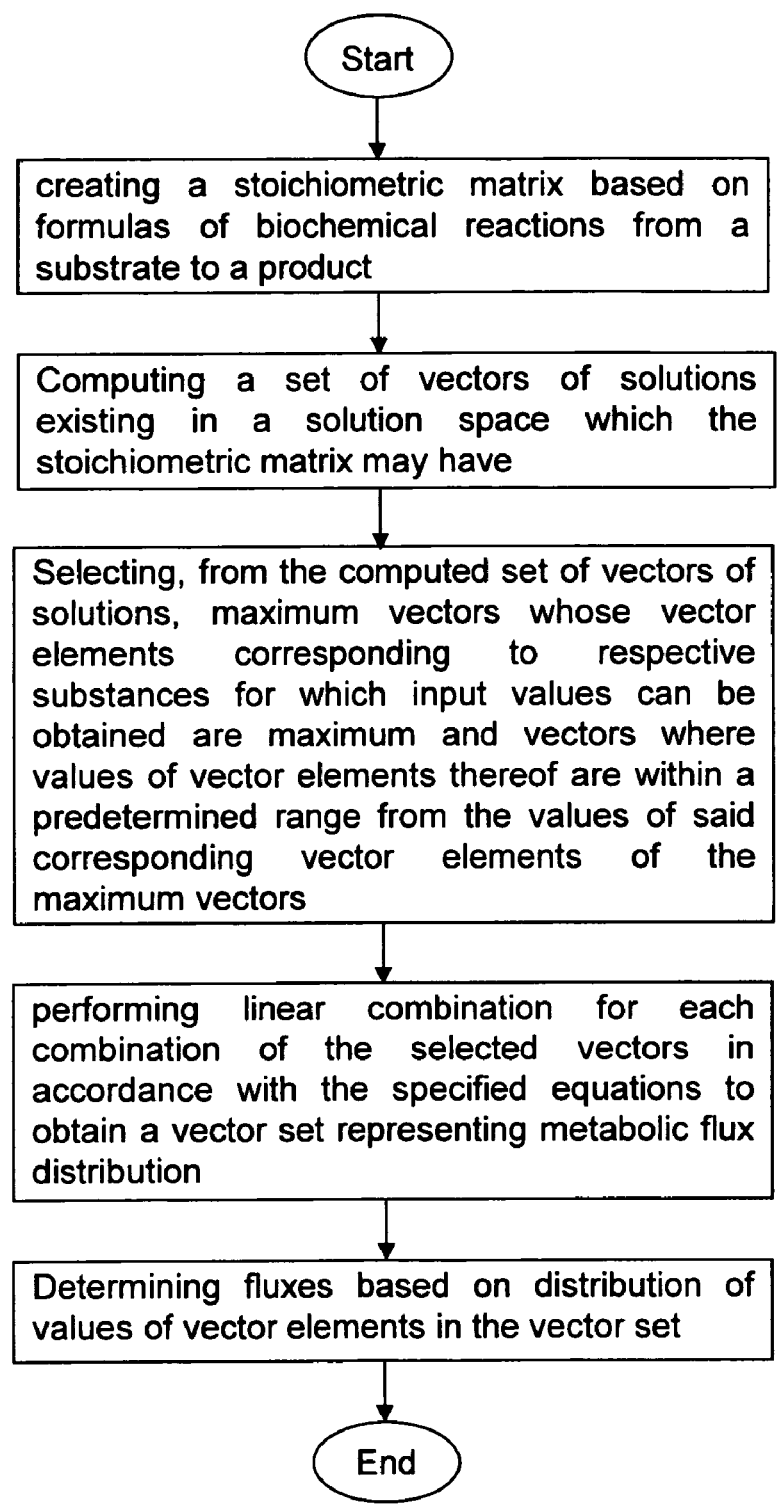
FIG. 6 shows a flowchart of another embodiment of the program of the present invention.

In the program of the present invention, it is also possible that, in the third step, vectors in which a value of any one of vector elements which are the same as the maximum vector elements shows a difference from the corresponding maximum value in the maximum vector within a predetermined range are selected in addition to the maximum vectors in which vector elements corresponding to respective substances for which input values can be obtained are maximum, then linear combination is performed in the same manner as that of the fourth step for each combination of the selected vectors to obtain a vector set representing metabolic flux distribution, and fluxes are determined based on distribution of values of vector elements in the vector set. A flowchart of the program of the present invention in such a case is shown in FIG. 6.

Further, the program according to the present invention can also be stored in a computer-readable recording medium. The term "recording medium" used herein includes arbitrary "removable physical media" such as Floppy (registered trade name) disc, magneto-optical disc, ROM, EPROM, EEPROM, CD-ROM, MO and DVD, arbitrary "fixed physical media" such as ROM, RAM and HD built in various computer systems and "communication media" for temporarily storing a program such as communication circuits and carrier waves for transmitting a program via a network represented by LAN, WAN and the Internet.

Further, the "program" is one for processing data written in an arbitrary language or operation notation, and its format such as source code or binary code is not limited. The "program" is not necessarily limited to a single program, and includes a program described in a distributed architecture comprising two or more modules or libraries or achieves its function by cooperating with a separate program represented by Operating System (OS). Well-known configurations and procedures can be used as specific configurations for reading the program stored in a recording medium, reading procedures, installation procedures after reading and so forth in each device shown in the embodiments.

The present invention is further described in detail by referent to examples.

REFERENCE EXAMPLE 1

(1) Construction of Metabolic Flux Analysis Model

A stoichiometric equation for calculating a metabolic flux was developed by assuming a quasi-steady state of intracellular metabolic intermediates (Savinell and Palsson, Journal of Theoretical Biology, 154, pp. 421-454, 1992; Vallino and Stephanopoulos, Biotechnology and Bioengineering, 41, pp. 633-646, 1993). Formulas of the reactions included in this model are as shown in Table 2. Explanations of the abbreviations are given in Table 1. Some reactions without branching were consolidated to simplify the formula. Since the pentose phosphate pathway is complicated, it was represented by using two formulas. For biomass composition, previously reported data was used (Neidhardt et al., Physiology of the Bacterial Cell, 1990). Further, the composition of amino acids in intracellular proteins was obtained from the concentration ratios of the amino acids obtained by actually hydrolyzing the intracellular proteins. The stoichiometric matrix of this model has a degree of freedom of 8, and 7 fluxes other than the sugar consumption rate must be determined to obtain a solution. The following 7 fluxes were defined as the free fluxes: bacterial cell production rate, lysine production rate, acetic acid production rate, formic acid production rate, ICL flux, G6PDH flux and malic enzyme flux. The results of the cell production rate and various production rates were obtained from the cultivation experiment. Further, the remaining 3 fluxes were determined by an optimization algorithm based on measured values of the isotope distributions in amino acids and so forth (described later). Further, the constructed model includes 14 reversible reactions. Their reversibilities were defined as exchange coefficients that can be represented by numerical values of 0 to 1 (Dauner et al., Biotechnology and Bioengineering, 76, pp. 144-156, 2001; Wiechert and de Graaf, Biotechnology and Bioengineering, 55, pp. 101-117, 1997). These exchange coefficients are also variables determined based on the measured values of the isotope distributions as the aforementioned 3 free fluxes. As for neighboring reactions in the glycolysis, pentose phosphate pathway and TCA cycle, the reversibilities were assumed to be equal for simplification. Since the results of sensitivity analysis revealed that the reactions 9, 29 and 30 in the reaction list of Table 2 had little influence on the isotope distributions, the values were assumed to be 0. From the above, reversible reactions of which exchange coefficients were to be determined were 6 reactions.

To calculate isotopomer distribution vectors (IDV) of all the substances in the model, an isotopomer balance equation was developed as a function of free fluxes and exchange coefficients and isotopomer distributions in substrates. A column vector called IDV represents proportions of isotopomers, and the sum of elements is 1 (Schmidt et al., Biotechnology and Bioengineering, 55, pp. 831-840, 1997; Wittmann and Heinzle, Biotechnology and Bioengineering, 62, pp. 739-750, 1999). The isotopomer balance equation is described by using an isotopomer mapping matrix (IMM) explained in more detail by Schmidt et al. (Schmidt et al., Biotechnology and Bioengineering, 55, pp. 831-840, 1997). An atom mapping matrix (AMM) is a matrix representing transfer of carbon atoms from a reactant to a product. Based on this, the isotopomer mapping matrix (IMM), which represents transfer of isotopomers from a reactant to a product, is computed by using MATLAB (The MathWorks, Natick, Mass.), which is a mathematical software.

The isotopomer balance equation can be solved by using the Gause-Seidel iteration method with the free fluxes and exchange coefficients as inputs.

In addition to consumption of glucose, a microbial cell takes up carbon dioxide and consumes acetic acid during the growth. Since carbon dioxide is also produced from metabolism of isotope-labeled glucose, some percentages of carbon dioxide consist of $^{13}C$-carbon dioxide. The percentage was calculated according to a carbon dioxide balance equation taking all the reactions producing carbon dioxide into consideration. Although accurate value varies depending on the intracellular metabolic flux distribution, it was generally about 32%. In this calculation, it was assumed that carbon dioxide from air was not consumed. This is because the concentration of carbon dioxide produced by the cells as a result of consumption of isotope-labeled glucose is very high (in the experiment, the concentration of exhausted carbon dioxide reached 4 to 5%), and therefore it may be considered that the total carbon dioxide partial pressure in a fermenter should be attributable to carbon dioxide exhausted from the cells.

Although isotopomer distributions cannot be obtained for all of the substances from the mass spectrometry analysis, mass distributions can be obtained. This information is represented as mass distribution vector (MDV), and each element includes an isotopomer having an identical mass (Wittman and Heinzle, Biotechnology and Bioengineering, 62, pp. 739-750, 1999). Therefore, for a substance having n of carbon atoms, MDV contains n+1 of elements. MDV can be calculated by adding up elements having an identical mass among those in IDV. To what degree the result of the model matches the experimental value can be evaluated by comparing the MDV calculated as described above with the MDV obtained from the experiment.

TABLE 1

| | |
|---|---|
| μ | Specific growth rate [$h^{-1}$] |
| ν | Specific sugar consumption rate [g/g/h] |
| ρ | Specific lysine production rate [g/g/h] |
| YE | Yeast extract |
| ldc | E. coli lysine decarboxylase gene (Constitutive) |
| cadA | E. coli lysine decarboxylase gene (Inducible) |
| lysC | E. coli aspartate kinase III gene |
| dapA | E. coli dihydrodipicolinate synthase gene |
| dapB | E. coli dihydrodipicolinate reductase gene |
| CT | Cultivation time |
| ICL | Isocitrate lyase |
| PP pathway | Pentose phosphate pathway |
| PEPC | Phosphoenolpyruvate carboxylase |
| ICD | Isocitrate dehydrogenase |
| DDH | meso-Diaminopimelate dehydrogenase |
| G6PDH | Glucose-6-phosphate dehydrogenase |
| 3PG | 3-Phospho-D-glyceric acid |
| AcCoA | Acetyl coenzyme A |
| AcOH | Acetic acid |
| aIVA | α-Keto-isovaleric acid |
| aKG | 2-Oxoglutaric acid |

TABLE 1-continued

| | |
|---|---|
| Ala | Alanine |
| Arg | Arginine |
| Asn | Asparagine |
| Asp | Aspartic acid |
| CHR | Chorismic acid |
| Cit | Citric acid |
| CO2 | Carbon dioxide |
| Cys | Cysteine |
| E4P | Erythrose-4-phosphate |
| extraC1 | Carbon atom derived from ATP curing histidine combination |
| F6P | Fructose-6-phosphate |
| Form | Formic acid |
| Fum | Fumaric acid |
| G6P | Glucose-6-phosphate |
| GAP | Glyceraldehyde-3-phosphate |
| Glc | Glucose |
| Gln | Glutamine |
| Glu | Glutamic acid |
| Gly | Glycine |
| His | Histidine |
| Ile | Isoleucine |
| Leu | Leucine |
| Lys | Lysine |
| Lysext | Lysine product (secreted) |
| Mal | Malic acid |
| Met | Methionine |
| mTHF | Methyltetrahydrofolic acid |
| NH3 | Ammonia |
| OAA | Oxaloacetatic acid |
| PEP | Phosphoenolpyruvic acid |
| Phe | Phenylalanine |
| Pro | Proline |
| PRPP | Phosphoribosyl pyrophosphate |
| Pyr | Pyruvic acid |
| R5P | Pentose phosphate pool |
| SDAP | N-Succinyl-L-2,6-diaminoheptanedioate |
| Ser | Serine |
| Suc | Succinic acid |
| THF | Tetrahydrofolic acid |
| Thr | Threonine |
| Trp | Tryptophan |
| Tyr | Tyrosine |
| Val | Valine |

TABLE 2

Reaction formulas used for metabolic model

| | | |
|---|---|---|
| [1] | | Glc + PEP -> G6P + Pyr |
| [2] | | G6P -> R5P + CO2 |
| [3] | (r) | 3R5P -> 2F6P + GAP |
| [4] | (r) | 2R5P -> F6P + E4P |
| [5] | (r) | G6P -> F6P |
| [6] | (r) | F6P -> 2GAP |
| [7] | (r) | GAP -> 3PG |
| [8] | (r) | 3PG -> PEP |
| [9] | (r) | PEP -> Pyr |
| [10] | | Pyr + CoA -> AcCoA + CO2 |
| [11] | (r) | PEP + CO2 -> OAA |
| [12] | | AcCoA -> AcOH + CoA |
| [13] | | AcCoA + OAA -> Cit + CoA |
| [14] | (r) | Cit -> aKG + CO2 |
| [15] | | aKG + NH$_3$ -> Glu |
| [16] | | aKG -> Suc + CO2 |
| [17] | | Cit + AcCoA -> Mal + Suc + CO2 + CoA |
| [18] | (r) | Succ -> Mal |
| [19] | (r) | Mal -> OAA |
| [20] | | OAA + Glu -> Asp + aKG |
| [21] | | Asp + Pyr -> Lys + CO2 |
| [22] | | Asp +Pyr + Glu -> Lys + aKG + CO2 |
| [23] | | Glu + NH3 -> Gln |
| [24] | | Glu -> Pro |
| [25] | | Glu + Gln + Asp + AcCoA + CO2 -> Arg + aKG + Fum + CoA |
| [26] | | Asp + Cys + mTHF -> Met + CoA + THF + Pyr + NH3 |
| [27] | | Asp -> Thr |
| [28] | | Thr + Glu + Pyr -> Ile + aKG + NH3 + CO2 |
| [29] | (r) | 3PG -> Ser |
| [30] | (r) | Ser + THF -> Gly + mTHF |
| [31] | | 2PEP + E4P -> CHR |
| [32] | | CHR + Glu -> Tyr + CO2 + aKG |
| [33] | | CHR + Glu -> Phe + CO2 + aKG |
| [34] | | CHR + R5P + Ser + Gln -> Trp + Glu + Pyr + CO2 + GAP |
| [35] | | 2Pyr -> aIVA + CO2 |
| [36] | | aIVA + Glu -> Val + aKG |
| [37] | | Val + Pyr -> Ala + aIVA |
| [38] | | aIVA + AcCoA + Glu -> Leu + CO2 + aKG + CoA |
| [39] | | PRPP + Gln + extraC1 -> His + aKG |
| [40] | | Ser + AcCoA + H2S -> Cys + AcOH |
| [41] | | Asp + NH3 -> Asn |
| [42] | (r) | Mal -> Pyr + CO2 |
| [43] | | R5P -> PRPP |
| [44] | | mTHF -> Form |
| [45] | | Gly -> CO2 + mTHF |
| [46] | | Ile + CO2 -> Thr + Pyr |

(r): Reversible reaction (2) Correction of Influences by Naturally Occurring Isotopes of Carbon, Hydrogen, Nitrogen and Oxygen Atoms A program was prepared according to the paper of Heizle et al. (Wittman and Heinzle, Biotechnology and Bioengineering, 62, pp. 739-750, 1999) and used to correct influences by naturally occurring isotopes of hydrogen, carbon, nitrogen and oxygen for the total analytical data.

The calculation was performed by using ratios of naturally occurring isotopes of carbon, hydrogen, nitrogen and oxygen, i.e., $^1H=0.99985$, $^2H=0.015$, $^{12}C=0.98893$, $^{13}C=0.01107$, $^{14}N=0.99634$, $^{15}N=0.00366$, $^{16}O=0.99759$, $^{17}O=0.00037$ and $^{18}O=0.00204$. Matrices for correction of naturally occurring isotopes of hydrogen, carbon and nitrogen can be described as follows, wherein α is an existing ratio of a low mass isotope, β is an existing ratio of a high mass isotope (these satisfy the condition of α+β=1), ρni is a corresponding binomial coefficient, and E1 is a substance name.

$$CMDV, E1 = \begin{pmatrix} \rho_{n1}*\alpha^n & 0 & 0 & \cdots \\ \rho_{n2}*\alpha^{n-1}*\beta^1 & \rho_{n1}*\alpha^n & 0 & \cdots \\ \rho_{n3}*\alpha^{n-2}*\beta^2 & \rho_{n2}*\alpha^{n-1}*\beta^1 & \rho_{n1}*\alpha^n & \cdots \\ \cdots & \cdots & \cdots & \cdots \end{pmatrix}$$

$$CMDV, ^{18}O = \begin{pmatrix} \rho_{n1}*\alpha^n & 0 & 0 & \cdots \\ 0 & \rho_{n1}*\alpha^n & 0 & \cdots \\ \rho_{n3}*\alpha^{n-2}*\beta^2 & 0 & \rho_{n1}*\alpha^n & \cdots \\ \cdots & \cdots & \cdots & \cdots \end{pmatrix}$$

(3) Optimization of Metabolic Flux

A program was constructed in which MDV was calculated by using the isotopomer balance equation with free fluxes and exchange reaction fluxes as input values, and the previously inputted values of free fluxes and exchange reaction fluxes were optimized by the evolutionary algorithm (Stephani et al, Journal of theoretical Biology, 199, pp. 45-61, 1999) so that the sum of squares of the difference from the MDV obtained by the experiment should be minimized. The variables to be optimized were fluxes of ICL, malic enzyme, pentose phosphate pathway (G6PDH), values of 6 exchange reactions and Pex, which represents exchange reactions of proteins and intracellular amino acid pools. The bacterial cell yield and lysine yield were set so that 20% deviation from the input values should be accepted in order to take measurement errors in the experiment into account. To reduce the computation time, some modifications were made in a general evolutionary algorithm. Since 50,000 elements and 200 generations were found to be optimal to search the minimum value in the space of solution as a result of various examinations, these set values were used for analyses.

(4) Sensitivity Analysis

The confidence interval of free flux depends not only on variance of measured values, but also on the Jacobian matrix. The Jacobian matrix shows degree of how easily each IDV changes when the free flux changes near the optimal value. The variance of measured values for amino acids was obtained from values obtained from 3 analyses. Based on these values, a sensitivity matrix was calculated according to the method of Mollney et al. (Biotechnology and Bioengineering, 66, pp. 86-103).

Before performing the cultivation experiment, sensitivity of the analysis model was analyzed to find the optimal mixing ratio of labeled glucose. When calculation was performed by limiting the labeled glucose to be used to 1-$^{13}$C-Glc and U-$^{13}$C-Glc, a mixing ratio of each 50% (mol %) was found to be optimal as a result.

(5) Cultivation Experiment

The bacterial strain, the plasmid, the seed culture medium, the main culture medium, and the feeding solution as described in Example 1 (3) below were used.

Cells of WYK050/pCAB1 strain were streaked on the LB agar medium, and were cultured as stationary culture at 37° C. for 24 hours. Cells from two of the stationary culture plates were inoculated into the initial medium. The seed culture was terminated when the initially added sugar was completely consumed, and the culture broth was inoculated to the main culture medium to perform the main culture. For the cultivation, a 1-L jar fermenter was used, and a labeled glucose (1-$^{13}$C-Glc:U-$^{13}$C-Glc=5:5) was used as the isotope substrate. The initial liquid volume of the culture was 300 ml, and the temperature and pH were regulated to be 37° C. and 6.7, respectively. Ammonia gas was used to regulate pH. Aeration was controlled at 300 ml/min. The stirring rate was suitably regulated so that the dissolved oxygen concentration of the culture broth should be always maintained at 5% or higher. Feeding of a glucose solution was started at 17 hours after the start of the cultivation. The feeding rate was suitably regulated so that the concentration of the remaining sugar in the medium should be 5 g/L or lower. A fermentation sample was obtained at 10 hours and at 25 hours after the start of the cultivation. The measurement of cell protein-hydrolyzed amino acids was also conduced for each sample for the purpose of correction. The measurement of isotope distribution in each amino acid was performed by using LC-MS.

(6) Metabolic Flux Analysis

By using the isotope distribution ratio of each amino acid obtained by the method of (5) mentioned above, metabolic fluxes were calculated according to the method of (3) mentioned above. The values of extracellular lysine production rate and acetic acid production rate as well as cell production rate standardized with the sugar consumption rate, which were used for the optimization of metabolic fluxes, are shown in Table 3.

Figure 4:
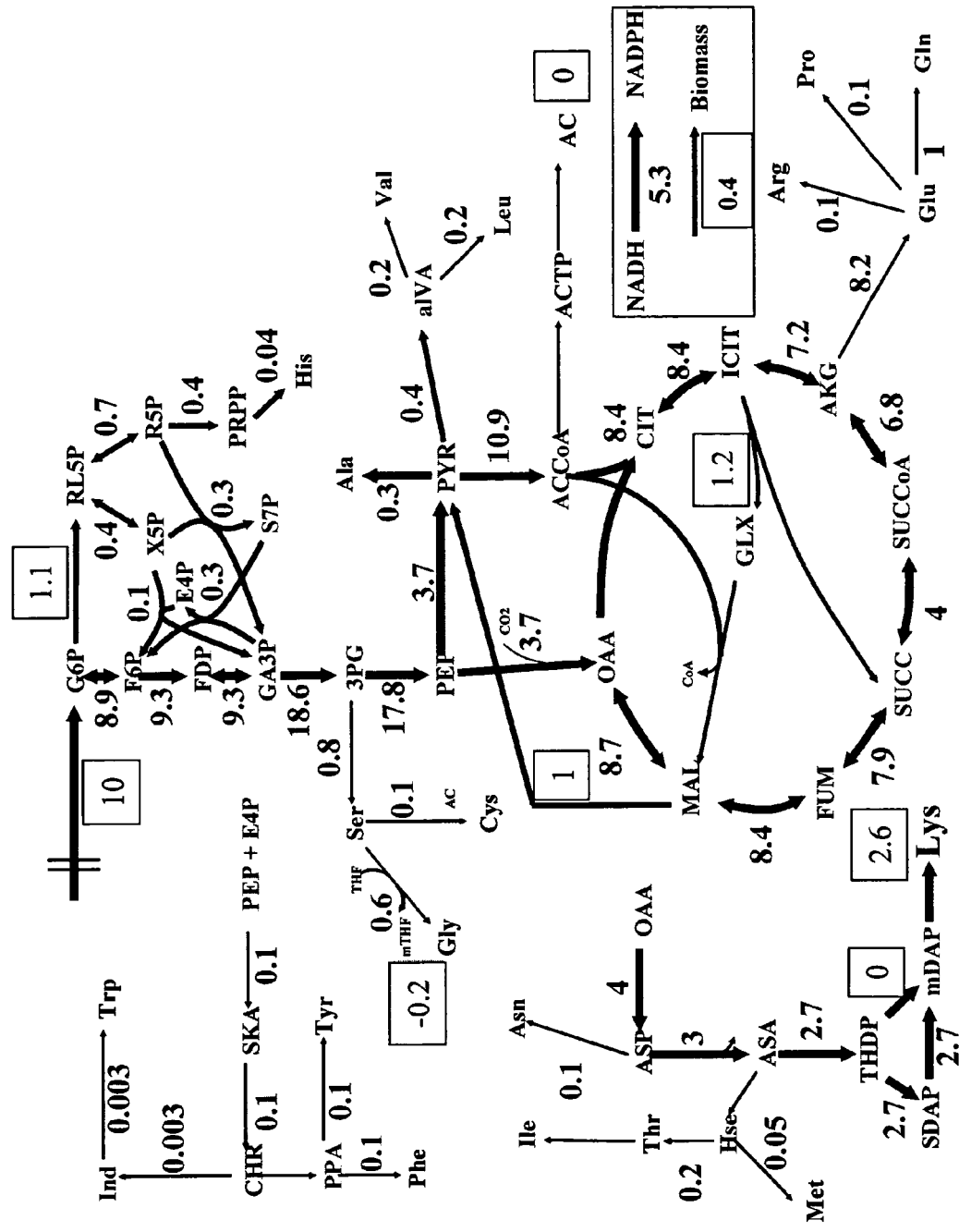
FIG. 4 shows metabolic flux distribution computed based on free flux data obtained after cultivation of 10 hours.

The free fluxes obtained as a result of the analyses at 10 hours and 25 hours after the start of cultivation are shown in Table 4, and metabolic flux distributions calculated based on the free fluxes at 10 hours after the start of cultivation are shown in FIG. 4.

TABLE 3

| CT | Biomass | Lys | AcOH |
|----|---------|-----|------|
| 10 | 0.36 | 0.29 | 0.0 |
| 25 | 0.26 | 0.28 | −0.24 |

* Unit of Biomass, AcOH and Lys is mmol/10 mmol-Glc
* CT represents cultivation time, of which unit is "hour".

TABLE 4

|  | At 17 hours from the start of cultivation | At 25 hours from the start of cultivation |
|---|---|---|
| Free flux |  |  |
| G6PDH | 1.103 | 0.701 |
| ICL | 1.189 | 5.853 |
| Malic Enzyme | 0.945 | 2.000 |
| Exchange coefficient |  |  |
| Pentose phosphate cycle | 0.187 | 0.232 |
| Glycolysis | 0.766 | 0.631 |
| PEPC | 0.004 | 0.000 |
| ICD | 0.000 | 0.000 |
| TCA cycle | 0.9 | 0.517 |
| Malic Enzyme | 0.000 | 0.184 |
| Pex (Protein degradation coefficient) | 0.009 | 0.008 |

EXAMPLE 1

(1) Creation of Stoichiometric Matrix

A stoichiometric equation for calculating a metabolic flux was constructed by assuming a quasi-steady state of intracellular metabolic intermediates (Savinell, J. M. and Palsson, B. O. J., Theor. Biol., 154:421-454, 1992; Vallino, J. J. and Stephanopoulos, G., Biotechnol. Bioeng., 41:633-646, 1993). The reaction formulas included in this model are as shown in Table 6. Descriptions of the abbreviations used in the present invention are listed in Table 5. Some reactions without branching were consolidated to simplify the formulas. Since the pentose phosphate pathway is complicated, it was represented by two formulas. Reported data was used for the component ratio of biomass (Neidhardt, F. C. et al., Physiology of the Bacterial Cell., Sinauer Associates, Massachusetts, 1990) and the biomass was represented by using the reaction formula [68].

TABLE 5

| 3PG | 3-Phospho-D-glyceric acid |
|-----|---------------------------|
| AcCoA | Acetyl coenzyme A |
| AcOH | Acetic acid |
| aIVA | A-Keto-isovaleric acid |
| aKG | 2-Oxoglutaric acid |
| Ala | Alanine |
| ALC | Acetohydroxy acid |
| Arg | Arginine |
| ASA | Aspartic acid semialdehyde |
| Asn | Asparagine |
| Asp | Aspartic acid |
| CHR | Chorismic acid |

TABLE 5-continued

| | |
|---|---|
| Cit | Citric acid |
| CO2 | Carbon dioxide |
| CoA | Coenzyme A |
| Cys | Cysteine |
| DDP | Dihydrodipicolinic acid |
| E4P | Erythrose-4-phosphate |
| F6P | Fructose-6-phosphate |
| FBP | Fructose bisphosphate |
| Form | Formic acid |
| Fum | Fumaric acid |
| G6P | Glucose-6-phosphate |
| GAP | Glyceraldehyde phosphate |
| Glc | Glucose |
| Gln | Glutamine |
| Glu | Glutamic acid |
| Gly | Glycine |
| Glyox | Glyoxylic acid |
| His | Histidine |
| Hse | Homoserine |
| Ile | Isoleucine |
| Ind | Indole glycerol phosphate |
| Isocit | Isocitric acid |
| Leu | Leucine |
| Lys | Lysine |
| Lysext | Lysine product (extracellular) |
| Mal | Malic acid |
| Met | Methionine |
| mDAP | meso-Diaminopimelic acid |
| mTHF | Methyl tetrahydrofolate |
| NH3 | Ammonia |
| OAA | Oxaloacetic acid |
| PEP | Phosphoenolpyruvic acid |
| Phe | Phenylalanine |
| PPA | Prephenic acid |
| Pro | Proline |
| PRPP | Phophoribosyl pyrophosphate |
| Pyr | Pyruvic acid |
| R5P | Ribose-5-phosphate |
| Ribu5P | Ribulose-5-phosphate |
| SDAP | N-Succinyl-L-2,6-diaminoheptanedioate |
| SKA | Shikimic acid |
| Sed7P | D-Sedoheptulose-7-phosphate |
| Ser | Serine |
| Suc | Succinic acid |
| SucCoA | Succinyl coenzyme A |
| THDP | Tetrahydrodipicolinic acid |
| THF | Tetrahydrofolic acid |
| Thr | Threonine |
| Trp | Tryptophan |
| Tyr | Tyrosine |
| Val | Valine |
| X5P | Xylulose-5-phosphate |

TABLE 6

List of used reaction formulas. Reversible reactions are marked with r.

| | | |
|---|---|---|
| [1] | | Glc + PEP --> G6P + Pyr |
| [2] | | G6P + 2NADP --> Ribu5P + 2NADPH + CO2 |
| [3] | r | Ribu5P --> R5P |
| [4] | r | Ribu5P --> X5P |
| [5] | r | X5P + R5P --> Sed7P + GAP |
| [6] | r | Sed7P + GAP --> E4P + F6P |
| [7] | r | X5P + E4P --> F6P + GAP |
| [8] | r | G6P --> F6P |
| [9] | r | F6P + ATP --> FBP + ADP |
| [10] | r | FBP --> 2GAP |
| [11] | r | GAP + NAD + ADP --> 3PG + NADH + ATP |
| [12] | r | 3PG --> PEP |
| [13] | | PEP + ADP --> Pyr + ATP |
| [14] | | Pyr + NAD + CoA --> AcCoA + NADH + CO2 |
| [15] | | PEP + CO2 --> OAA |
| [16] | | AcCoA + ADP --> AcOH + ATP + CoA |
| [17] | | AcCoA + OAA --> Cit + CoA |
| [18] | r | Cit --> Isocit |
| [19] | r | Isocit + NADP --> aKG + NADPH + CO2 |
| [20] | | aKG + NADPH + NH3 --> Glu + NADP |
| [21] | | aKG + NAD + CoA --> SucCoA + NADH + CO2 |
| [22] | r | SucCoA + ADP --> Suc + ATP + CoA |
| [23] | r | Suc + FAD --> Fum + FADH |
| [24] | r | Fum --> Mal |
| [25] | r | Mal + NAD --> OAA + NADH |
| [26] | | OAA + Glu --> Asp + aKG |
| [27] | | Asp + ATP + NADPH --> ASA + ADP + NADP |
| [28] | | ASA + Pyr --> DDP |
| [29] | | DDP + NADPH --> THDP + NADP |
| [30] | | THDP + SucCoA + Glu --> SDAP + aKG + CoA |
| [31] | | SDAP --> mDAP + Suc |
| [32] | | mDAP --> Lys + CO2 |
| [33] | r | Glu + ATP + NH3 --> Gln + ADP |
| [34] | | Glu + 2NADPH + ATP --> Pro + 2NADP + ADP |
| [35] | | Glu + 5ATP + NADPH + Gln + Asp + AcCoA + CO2 --> Arg + 5ADP + NADP + aKG + Fum |
| [36] | | ASA + NADPH --> Hse + NADP |
| [37] | | Hse + SucCoA + Cys + mTHF --> Met + Suc + CoA + THF + Pyr + NH3 |
| [38] | | Hse + ATP --> Thr + ADP |
| [39] | | Thr + Glu + NADPH + Pyr --> Ile + aKG + NADP + NH3 + CO2 |
| [40] | r | 3PG --> Ser |
| [41] | r | Ser + THF --> Gly + mTHF |
| [42] | r | PEP + E4P + NADPH --> SKA + NADP |

TABLE 6-continued

List of used reaction formulas. Reversible reactions are marked with r.

| | | |
|---|---|---|
| [43] | | CHR --> PPA |
| [44] | | PPA + NAD + Glu --> Tyr + NADH + CO2 + Akg |
| [45] | | PPA + Glu --> Phe + CO2 + aKG |
| [46] | | CHR + R5P + 2ATP + Gln --> Ind + Glu + Pyr + CO2 + GAP + 2ADP |
| [47] | | 2Pyr --> ALC |
| [48] | | aIVA + Glu --> Val + aKG |
| [49] | | Val + Pyr --> ALA + aIVA |
| [50] | | aIVA + AcCoA + NAD + Glu --> Leu + NADH + CO2 + aKG + CoA |
| [51] | | PRPP + ATP + Gln + Glu + 2NAD --> His + ADP + Glu + aKG + 2NADH |
| [52] | | Ser + AcCoA + H2S --> Cys + AcOH |
| [53] | | SKA + PEP + ATP --> CHR + ADP |
| [54] | | Ind + Ser --> Trp |
| [55] | | ALC + NADPH --> aIVA + NADP + CO2 |
| [56] | r | NADH --> NADPH |
| [57] | | 2NADH + O2 + 2ADP --> 2ATP + 2NAD |
| [58] | | 2FADH + O2 + ADP --> ATP + 2FAD |
| [59] | r | Asp + 2 ATP + NH3 --> Asn + 2 ADP |
| [60] | | Isocit --> Glyox + Succ |
| [61] | | AcCoA + Glyox --> Mal + CoA |
| [62] | | Mal + NAD --> Pyr + CO2 + NADH |
| [63] | r | R5P + 2 ATP --> PRPP + 2 ADP |
| [64] | | mTHF + NADP --> NADPH + THF + Form |
| [65] | | NAD + Gly + THF --> mTHF + NADH + CO2 + NH3 |
| [66] | | ATP --> ADP |
| [67] | | Lys --> Lysext |
| [68] | | Biomass combination (described below) |
| | | RNA (21.33%) |
| | | 3.47 PRPP + 5.02 Gln + −5.02 Glu + 3.08 Gly + 6.17 Asp + 32.41 |
| | | ATP + −32.41 ADP + 6.17 mTHF + −6.17 THF + 3.09 NAD + −3.09 |
| | | NADH + 6.17 NADP + −6.17 NADPH + 1.16 CO2 + −3.47 |
| | | Fum + −3.86 NH3 |
| | | DNA (3.23%) |
| | | 3.37 PRPP + 4.88 Gln + −4.88 Glu + 3 Gly + 6 Asp + 31.5 ATP + −31.5 |
| | | ADP + 7.12 mTHF + −7.12 THF + 3 NAD + −3 NADH + 3.75 NADP + −3.75 |
| | | NADPH + 1.12 CO2 + −3.37 Fum + −3.75 NH3 |
| | | Phospholipid (9.47%) |
| | | 20.8 AcCoA + −20.8 CoA + 1.95 GAP + 0.65 Ser + 44.2 ATP + −44.2 |
| | | ADP + 38.35 NADH + −38.35 NAD + −0.65 CO2 |
| | | Peptidoglycan (2.60%) |
| | | 1.94 F6P + 1.94 AcCoA + −1.94 CoA + 1.94 Gln + −1.94 Glu + 2.91 |
| | | Ala + 0.97 PEP + 0.97 Lys + 6.97 ATP + −6.97 ADP + 0.97 NADPH + −0.97 |
| | | NADP + −0.97 CO2 |
| | | Lipopolysaccharide (3.54%) |
| | | 0.91 R5P + 0.91 F6P + 0.91 PEP + 15.47 AcCoA + −0.91 AcOH + −0.91 |
| | | Glu + 0.91 Gln + 32.76 ATP + 12.74 NADH |
| | | Protein (57.23%) |
| | | 0.77 Gly + 0.96 Ala + 0.67 Val + 0.85 Leu + 0.44 Ile + 0.44 Ser + 0.48 |
| | | Thr + 0.30 Phe + 0.26 Tyr + 0.01 Trp + 0.15 Cys + 0.22 |
| | | Met + 0.54 Lys + 0.46 Arg + 0.16 His + 0.46 Asp + 0.52 Glu + 0.46 |
| | | Asn + 0.52 Gln + 0.34 Pro |
| | | Glycogen (2.60%) |
| | | F6P + ATP |

(2) Calculation Based on Elementary Mode

By using FluxAnalyzer (developed by Steffen Klamt, the Max-Planck-Institute of Dynamics of Complex Technical Systems), the aforementioned stoichiometric equations were inputted, and elementary modes of the models were analyzed (Klamt et al., Bioinformatics 19(2):261-269, 2003). The obtained elementary modes were 852. The values of lysine production and cell production in the modes giving the maximum lysine production and cell production among them were 8.52 mmol/10 mmol-Glc and 1.16 g/10 mmol-Glc, respectively. Further, the value of emitted carbon dioxide in the mode giving the maximum emitted carbon dioxide was 60 mmol/10 mmol-Glc.

(3) Metabolic Flux Analysis Using Experimental Data

The bacterial strains and media shown below were used.

(a) *Escherichia coli* Strain and Plasmid

Bacterial strain: WYK050 (a strain derived from *Escherichia coli* wild strain W3110, which is resistant to S-(2-aminoethyl)cysteine and deficient in lysine decomposition genes, ldc and cadA genes (Kikuchi, Y. et al. J. Bacteriol., 179, pp. 4486-4492, 1997))

Plasmid: pCAB1 (obtained by incorporating lysC, dapA and dapB genes derived from *Escherichia coli* into vector RSF1010)

A bacterial strain obtained by introducing pCAB1 into WYK050 was used for cultivation.

(b) Media

LB agar medium: 1.0% Bacto tryptone, 0.5% Bacto yeast extract, 1% NaCl, 1.5% agar. If necessary, 20 μg/ml of streptomycin was added.

Main culture medium: 16 g/L of ammonium sulfate, 3 g/L of potassium dihydrogenphosphate, 4 g/L of yeast extract, 10 mg/L of iron sulfate heptahydrate, 10 mg/L of manganese sulfate pentahydrate, 400 mg/L of isoleucine, 40 g/L of glucose, 1 g/L of magnesium sulfate heptahydrate. pH was adjusted to 7.0 with potassium hydroxide. If necessary, 20 µg/ml of streptomycin was added. The main culture medium was used for liquid culture of *Escherichia coli*.

Feeding solution: 500 g/L of glucose, 80 g/L of ammonium sulfate

Cultivation Experiment

A suspension of cells of the WYK050/pCAB1 strain was streaked on the LB agar medium, and the cells were cultured as stationary culture at 37° C. for 24 hours. Cells from two of the stationary culture plates were inoculated into the seed culture medium. The seed culture was terminated when the initially added sugar was completely consumed, and the culture broth was inoculated to the main culture medium to perform the main culture. The same medium composition was used for the seed culture and the main culture, and it was the composition described above as the main culture medium. For the cultivation, a 1-L jar fermenter was used, and glucose was used as the substrate. The initial liquid volume of the cultivation was 300 ml, and the temperature and pH were regulated to be 37° C. and 6.7, respectively. Ammonia gas was used to regulate pH. Aeration was controlled at 300 ml/min. The stirring rate was suitably regulated so that the dissolved oxygen concentration of the culture broth should be always maintained at 5% or higher. Feeding of a sugar solution (feeding solution) was started at 17 hours after the start of the cultivation. The feeding rate was suitably regulated so that the sugar concentration in the medium should be 5 g/L or lower. Fermentation samples were obtained in suitable intervals. The lysine concentration was measured by using an amino acid analyzer (HITACHI L-8500). As to cell mass, OD at 620 nm was measured. The time-course profiles are shown in FIG. 1.

Figure 2:
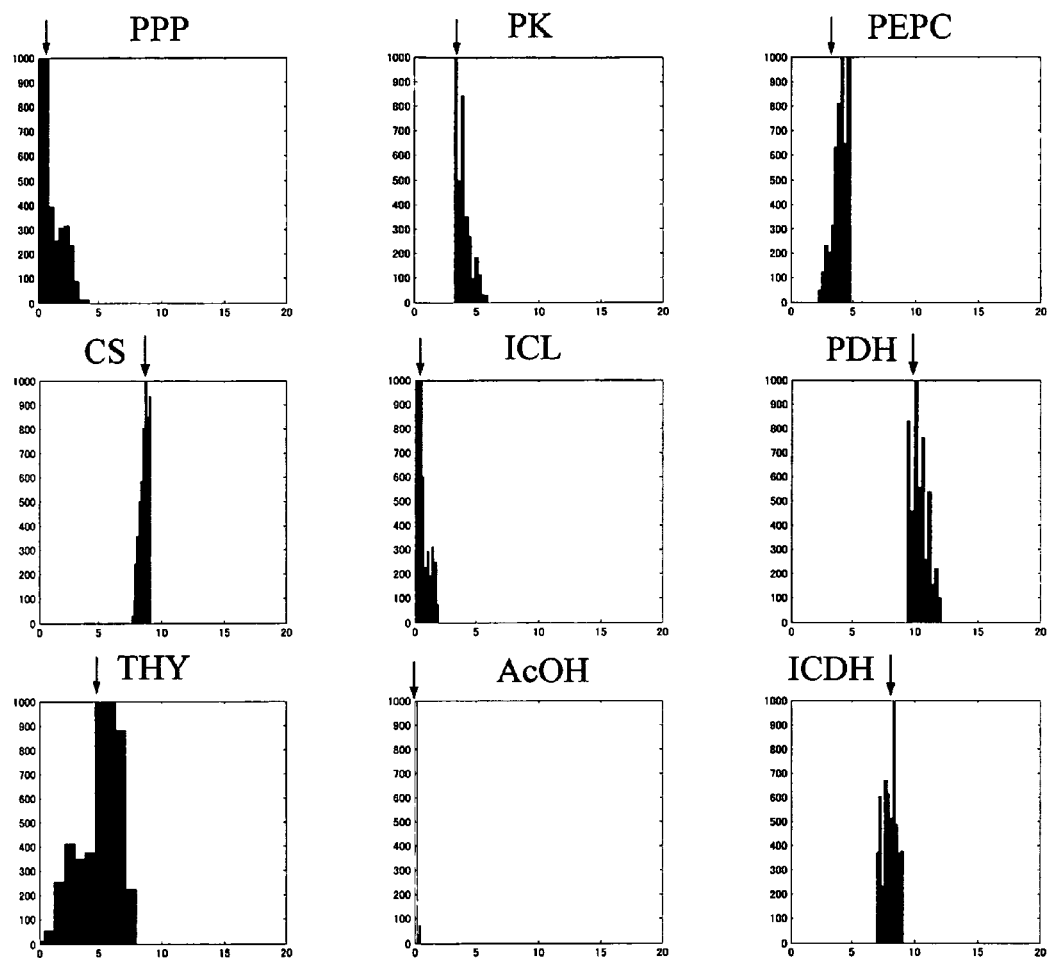
FIG. 2 shows metabolic flux distribution obtained with a permitted deviation range of 4%.
Figure 3:
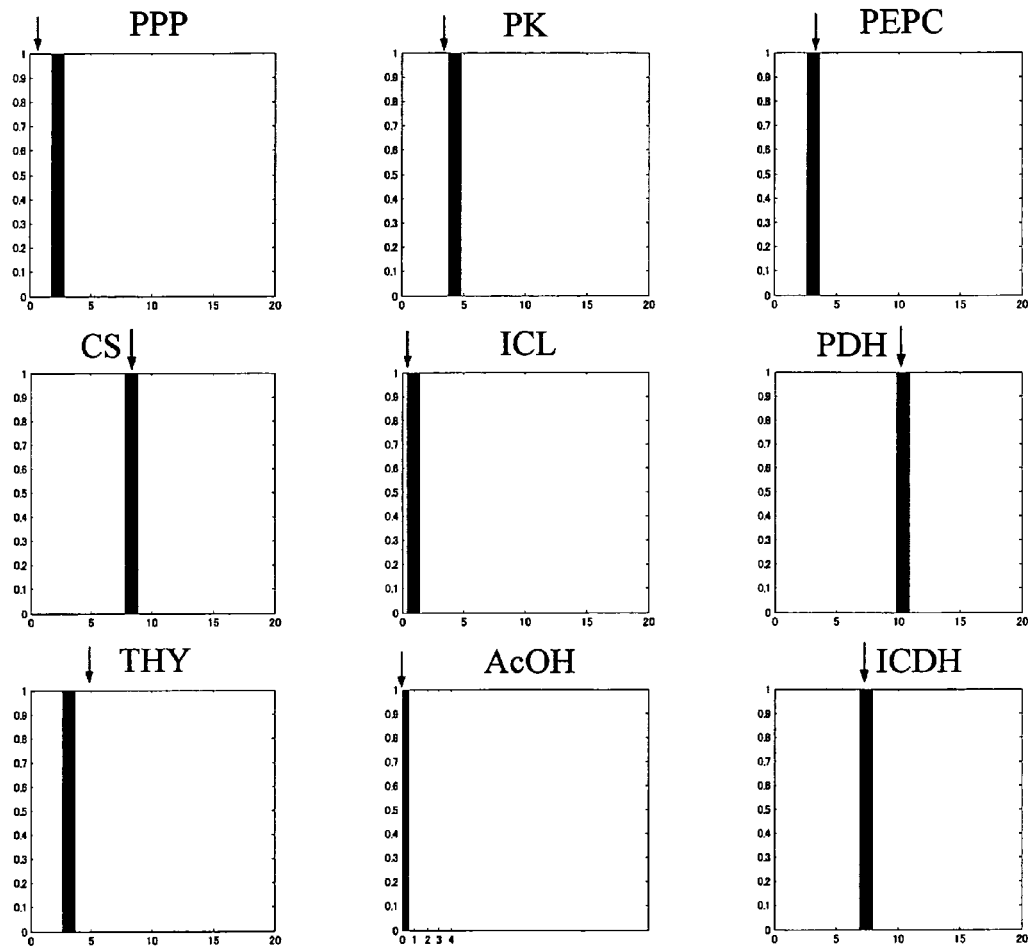
FIG. 3 shows metabolic flux distribution obtained with a permitted deviation range of 0%.

The data obtained after a cultivation time of 10 hours were used among the results of the cultivation to compute metabolic fluxes. Three kinds of data, specific growth rate=0.364 (g/10 mmol-Glc) and lysine production rate=2.88 (mmol/10 mmol-Glc) as well as emitted carbon dioxide=26.2 (mmol/10 mmol-Glc) calculated from the foregoing values with presupposing that the outputted carbon consisted of carbon dioxide except for the cells and lysine, were used as the input values. Coefficients obtained by dividing the input values with the maximum values of the vector elements obtained in (2) mentioned above were each multiplied on a corresponding maximum vector (elementary mode), and linear combination of the vectors was performed to compute flux vectors. In this operation, a permitted deviation range of 4% with respect to each of the maximum vectors of the vectors used for the linear combination was used to compute possible flux vectors. That is, the linear combination was also performed by using each of vectors of which vector element values had a difference within the permitted deviation range with respect to the maximum fluxes (vector elements) corresponding to the input values, of vectors giving the maximum values, to compute flux vectors. The results are shown in FIG. 2, in which fluxes in the computed flux vectors are indicated as distribution. The horizontal axis of the graph represents the flux, and the vertical axis represents frequency of appearance. The arrows indicate the results obtained by the metabolic flux analysis performed by the method described in Reference Example 1. Further, the results obtained from computation using a permitted deviation range with respect to each maximum vector of 0% are shown in FIG. 3.

The computation results obtained by the method of the present invention extremely well conformed to the results of the metabolic flux analysis performed by using the isotope-labeled substrate described in Reference Example 1. Although a part of the reaction formulas used for the construction of the metabolic models in Reference Example 1 are different from those used in Example 1, this is because two or more reactions that can be summarized as one reaction were described as one reaction for simplification in Reference Example 1 in order to avoid complicated computation. It was confirmed that this simplification did not provide any substantial difference in the results. From the results mentioned above, it was found that metabolic flux distribution in a model could be computed only from cultivation data such as cell production rate and objective product production rate according to this method.

What is claimed is:

1. A method for determining a vector representing metabolic flux distribution of a cell, on a sufficiently programmed computer, comprising:

creating a stoichiometric matrix based on formulas of biochemical reactions from a substrate to a product;

computing a set of vectors of solutions existing in a stoichiometric matrix solution space;

selecting, from the set of vectors of solutions, maximum vectors whose vector elements correspond to maximum input values for respective substances input values;

performing a linear combination for the selected vectors in accordance with the following equations to obtain a vector representing metabolic flux distribution:

$$S_{flux} = \sum_{i=1}^{n} a_i \cdot p_i \cdot S(i) + \sum_{i=1}^{n} b_i \cdot q_i \cdot A(i) \quad (I)$$

$$\sum_{i=1}^{n} a_i + \sum_{i=1}^{n} b_i = 1 \quad (II)$$

$S_{flux}$: vector representing metabolic flux distribution to be determined,

S(i): vector selected for substance for which inputted value can be obtained,

A(i): adjustment vector, a, b: coefficients for linear combination (b may be 0), p: coefficient for obtaining consistency with input value as numerical value, q: coefficient of adjustment vector, and identifying and displaying the vector representing metabolic flux distribution.

2. A method for determining distribution of fluxes of a cell, on a sufficiently programmed computer, comprising:

creating a stoichiometric matrix based on formulas of biochemical reactions from a substrate to a product;

computing a set of vectors of solutions existing in a stoichiometric matrix solution space;

selecting, from the set of vectors of solutions, maximum vectors whose vector elements correspond to maximum input values for respective substances and vectors where values of vector elements thereof are within a predetermined range from the values of said corresponding vector elements of the maximum vectors;

performing a linear combination for each combination of the selected vectors in accordance with the following equations to obtain a vector set representing metabolic flux distribution:

$$S_{flux} = \sum_{i=1}^{n} a_i \cdot p_i \cdot S(i) + \sum_{i=1}^{n} b_i \cdot q_i \cdot A(i) \quad (I)$$

$$\sum_{i=1}^{n} a_i + \sum_{i=1}^{n} b_i = 1 \quad (II)$$

$S_{flux}$: vector representing metabolic flux distribution to be obtained, $S(i)$: vector selected for substance for which input value can be obtained, $A(i)$: adjustment vector, a, b: coefficients for linear combination (b may be 0), p: coefficient for obtaining consistency with input value as numerical value, q: coefficient of adjustment vector, determining distribution of values of vector elements in the vector set, and identifying and displaying the determined distribution.

3. The method according to claim 1, wherein the step of computing a set of vectors of solutions existing in the solution space which the stoichiometric matrix can have is performed by computation based on elementary mode.

4. The method according to claim 1, wherein the substances for which input values can be obtained include carbon dioxide.

5. The method according to claim 4, wherein the substances for which input values can be obtained consist of an objective product, biomass, carbon dioxide and byproduct, and the linear combination is performed in accordance with the following equations:

$$S_{flux} = \alpha_1 \cdot \text{product} + \alpha_2 \cdot \text{Biomass} + \alpha_3 \cdot CO_{2\max} + \sum_{i=1}^{n} \beta_i \cdot \text{byproduct}(i)$$

$$\sum_{i=1}^{3} \alpha_i + \sum_{i=1}^{n} \beta_i = 1$$

$S_{flux}$: vector representing metabolic flux distribution to be determined, product: vector selected for objective product (multiplied by coefficient for obtaining consistency with input value), biomass: vector selected for cell (multiplied by coefficient for obtaining consistency with input value), $CO_2$: vector selected for carbon dioxide (multiplied by coefficient for obtaining consistency with input value), byproduct (i): vector selected for byproduct (multiplied by coefficient for obtaining consistency with input value), $\alpha_i$: coefficient for linear combination, $\beta_i$: coefficient for linear combination.

6. The method according to claim 2, wherein the substances for which input values can be obtained include carbon dioxide.

7. The method according to claim 6, wherein the substances for which input values can be obtained consist of an objective product, biomass, carbon dioxide and by product, and the linear combination is performed in accordance with the following equations:

$$S_{flux} = \alpha_1 \cdot \text{product} + \alpha_2 \cdot \text{Biomass} + \alpha_3 \cdot CO_{2\max} + \sum_{i=1}^{n} \beta_i \cdot \text{byproduct}(i)$$

$$\sum_{i=1}^{3} \alpha_i + \sum_{i=1}^{n} \beta_i = 1$$

$S_{flux}$: vector representing metabolic flux distribution to be determined, product: vector selected for objective product (multiplied by coefficient for obtaining consistency with input value), biomass: vector selected for cell (multiplied by coefficient for obtaining consistency with input value), $CO_2$: vector selected for carbon dioxide (multiplied by coefficient for obtaining consistency with input value), byproduct (i): vector selected for byproduct (multiplied by coefficient for obtaining consistency with input value), $\alpha_i$: coefficient for linear combination, $\beta_i$: coefficient for linear combination.

8. The method according to claim 3, wherein the substances for which input values can be obtained include carbon dioxide.

9. The method according to claim 8, wherein the substances for which input values can be obtained consist of an objective product, biomass, carbon dioxide and by product, and the linear combination is performed in accordance with the following equations:

$$S_{flux} = \alpha_1 \cdot \text{product} + \alpha_2 \cdot \text{Biomass} + \alpha_3 \cdot CO_{2\max} + \sum_{i=1}^{n} \beta_i \cdot \text{byproduct}(i)$$

$$\sum_{i=1}^{3} \alpha_i + \sum_{i=1}^{n} \beta_i = 1$$

$S_{flux}$: vector representing metabolic flux distribution to be determined, product: vector selected for objective product (multiplied by coefficient for obtaining consistency with input value), biomass: vector selected for cell (multiplied by coefficient for obtaining consistency with input value), $CO_2$: vector selected for carbon dioxide (multiplied by coefficient for obtaining consistency with input value), byproduct (i): vector selected for byproduct (multiplied by coefficient for obtaining consistency with input value), $\alpha_i$: coefficient for linear combination, $\beta_i$: coefficient for linear combination.

10. The method according to claim 2, wherein the step of computing a set of vectors of solutions existing in the solution space which the stoichiometric matrix can have is performed by computation based on elementary mode.

11. The method according to claim 10, wherein the substances for which input values can be obtained include carbon dioxide.

12. The method according to claim 11, wherein the substances for which input values can be obtained consist of an objective product, biomass, carbon dioxide and by product, and the linear combination is performed in accordance with the following equations:

$$S_{flux} = \alpha_1 \cdot \text{product} + \alpha_2 \cdot \text{Biomass} + \alpha_3 \cdot CO_{2max} + \sum_{i=1}^{n} \beta_i \cdot \text{byproduct}(i)$$

$$\sum_{i=1}^{3} \alpha_i + \sum_{i=1}^{n} \beta_i = 1$$

$S_{flux}$: vector representing metabolic flux distribution to be determined, product: vector selected for objective product (multiplied by coefficient for obtaining consistency with input value), biomass: vector selected for cell (multiplied by coefficient for obtaining consistency with input value), $CO_2$: vector selected for carbon dioxide (multiplied by coefficient for obtaining consistency with input value), byproduct (i): vector selected for byproduct (multiplied by coefficient for obtaining consistency with input value), $\alpha_i$: coefficient for linear combination, $\beta_i$: coefficient for linear combination.

* * * * *